United States Patent [19]
Martindale et al.

[11] Patent Number: 5,043,502
[45] Date of Patent: Aug. 27, 1991

[54] PRODUCTION OF XYLENES FROM LIGHT ALIPHATIC HYDROCARBONS VIA DEHYDROCYCLODIMERIZATION AND METHYLATION

[75] Inventors: David C. Martindale, Roselle; Paul J. Kuchar, Hinsdale, both of Ill.

[73] Assignee: UOP, Des Plaines, Ill.

[21] Appl. No.: 494,383

[22] Filed: Mar. 16, 1990

[51] Int. Cl.$^5$ .............................................. C07C 2/68
[52] U.S. Cl. ..................................... 585/323; 585/467
[58] Field of Search ............................. 585/323, 467

[56] References Cited

U.S. PATENT DOCUMENTS

| | | | |
|---|---|---|---|
| 3,761,389 | 9/1973 | Rollmenn | 585/323 |
| 4,283,306 | 8/1981 | Herkes | 252/432 |
| 4,377,718 | 3/1922 | Sato et al. | 585/467 |
| 4,444,989 | 4/1984 | Herkes | 467/585 |
| 4,528,412 | 7/1985 | Steacy | 585/415 |
| 4,634,799 | 1/1987 | Haun et al. | 585/415 |
| 4,636,483 | 1/1987 | Kjell et al. | 502/61 |
| 4,642,402 | 2/1987 | Jensen | 585/411 |
| 4,677,235 | 6/1987 | Mowry | 585/415 |
| 4,851,602 | 7/1989 | Harandi et al. | 585/323 |
| 4,935,574 | 6/1990 | D'Amore et al. | 585/467 |

OTHER PUBLICATIONS

*Cyclar, One Step Processing of LPG to Aromatics and Hydrogen*, R. F. Anderson et al.

*Primary Examiner*—Curtis R. Davis
*Attorney, Agent, or Firm*—Thomas K. McBride; John G. Tolomei; John G. Cutts, Jr.

[57] ABSTRACT

Aromatic hydrocarbons containing controlled proportions of xylene isomers and benzene may be produced by a process combining dehydrocyclodimerization of $C_2$-$C_5$ aliphatic hydrocarbons, separation of benzene and toluene, and selective methylation.

14 Claims, 2 Drawing Sheets

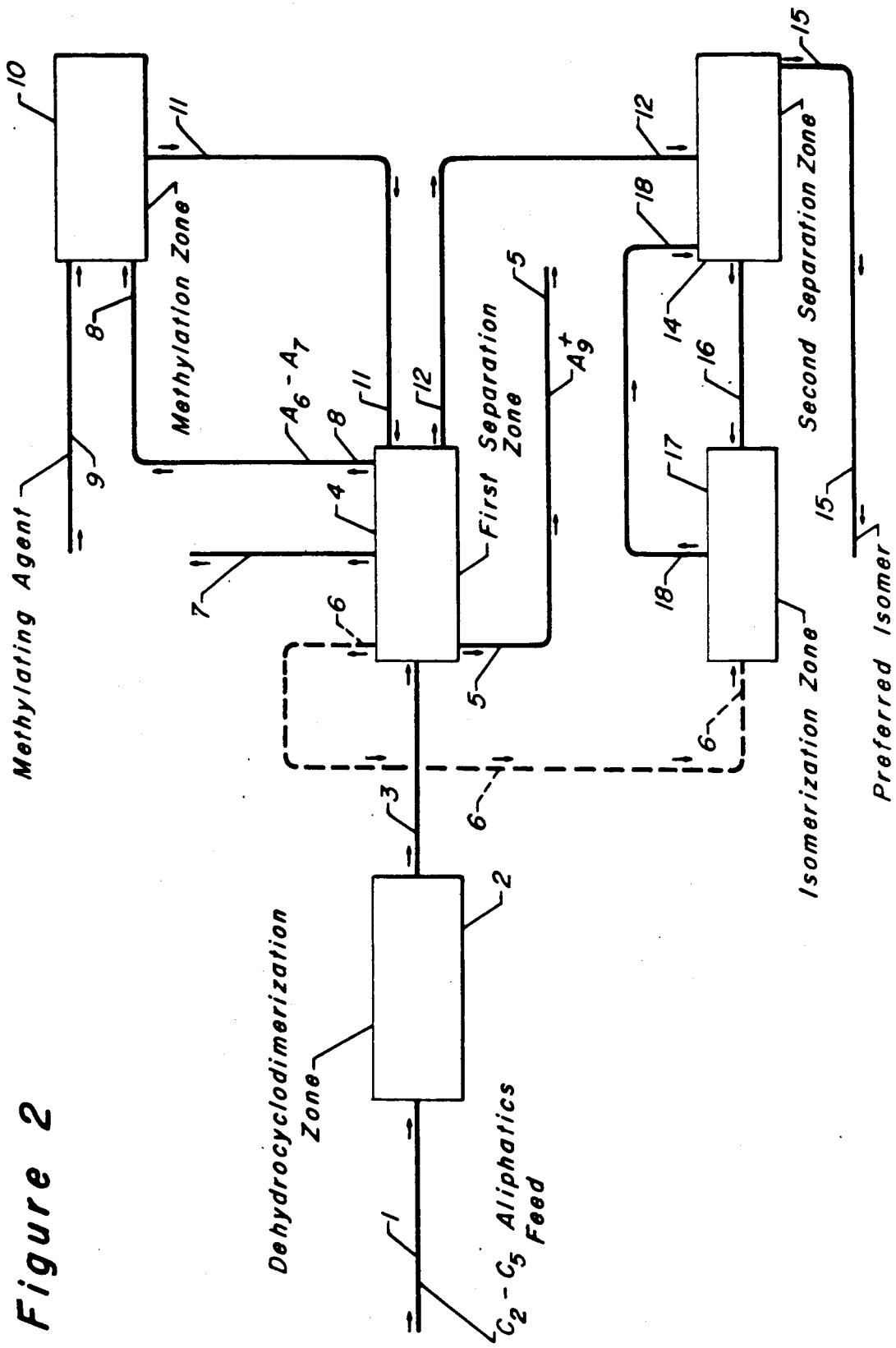

PRODUCTION OF XYLENES FROM LIGHT ALIPHATIC HYDROCARBONS VIA DEHYDROCYCLODIMERIZATION AND METHYLATION

FIELD OF THE INVENTION

The subject process relates to a hydrocarbon conversion process wherein $C_2-C_5$ aliphatic hydrocarbons are converted to aromatic hydrocarbons containing an abundance of selected xylene isomers. The subject process also relates to a catalytic-process referred to as dehydrocyclodimerization (DHCD) wherein two or more molecules of a light aliphatic-hydrocarbon, such as propane, are joined together to form a product aromatic-hydrocarbon. The subject process also relates to a process referred to as selective toluene methylation wherein a methyl group from a methylating agent, such as methanol, is joined to toluene to create a preferred $C_8$ aromatic-hydrocarbon isomer.

INFORMATION DISCLOSURE

Most aromatics production is based on recovery of aromatics derived from catalytic reforming of naphtha. That process, using a feed with a boiling range higher than that of $C_2-C_5$ hydrocarbons, produces benzene, toluene, relatively large amounts of xylenes, and heavier aromatics. The products may be separated by distillation and selective adsorption processes. The aromatics produced by reforming may be converted to other aromatics by isomerization of $C_8$ hydrocarbons, alkylation of alkyl aromatics, dealkylation of alkyl aromatics, or transalkylation of alkyl aromatics. An aromatics plant may combine such processes as needed to provide the desired distribution of products. Many patents disclose processes for the dehydrocyclodimerization of $C_2-C_5$ aliphatic hydrocarbons to aromatics. Recent patents which disclose the process generally include U.S. Pat. Nos. 4,528,412; 4,634,799; 4,642,402; and, 4,677,235. The discussion of the prior art in such patents suggests that there has been considerable interest in these processes and that the catalysts are likely to employ various forms of what are often called "molecular sieves". The present invention does not require any specific catalyst but the catalysts comprising phosphorous containing alumina, a gallium component, and a zeolite catalyst as suggested in U.S. Pat. No. 4,636,483 are of particular interest.

The process of selective toluene methylation has been disclosed in such patents as U.S. Pat. Nos. 4,283,306 and 4,444,989. Typically, toluene is converted to mixed xylenes by contact with a methylating compound such as methanol or methyl ether over a suitable catalyst, such as molecular sieves, which may contain metallic catalytic components. The present invention is not specific to any one of such catalysts, although the catalysts such as the crystalline silica disclosed by DuPont are considered especially useful.

The combination of dehydrocyclodimerization with transalkylation was suggested in a paper delivered to the Spring National Meeting of the A.I. Ch. E. at Houston, Tx. in 1985. *Cyclar, One Step Processing of LPG to Aromatics and Hydrogen*. R. F. Anderson et al. In this paper Anderson suggests using transalkylation to convert toluene produced by dehydrocyclodimerization in order to increase the yield of both benzene and toluene.

The cited prior art does not suggest the combination of dehydrocyclodimerization in an integrated flow-scheme with selective toluene methylation. Further, the prior art does not teach the practice of selectively methylating toluene with benzene as a diluent. Both U.S. Pat. Nos. 4,444,989 and 4,377,718 disclose staged addition of the methylating agent as a means of limiting concentration and suggest the use of hydrogen gas as a diluent.

SUMMARY OF THE INVENTION

The invention is a process flow scheme for the production of xylenes and benzene from light aliphatic hydrocarbons which includes a dehydrocyclodimerization section, a first separation zone which serves the dual purpose of recovering benzene and toluene and isolating $C_8$ aromatics, and a selective toluene methylation section. Aromatic hydrocarbons containing a controlled proportion of xylene isomers and benzene may be produced by a process combining dehydrocyclodimerization of $C_2-C_5$ aliphatic hydrocarbons, separation of benzene and toluene, and selective toluene methylation. The object of the invention is to increase the amount of xylene and a preferred $C_8$ aromatic isomer which is produced without significantly increasing the amount of benzene produced. There are two main advantages for this flow scheme. One lies in the flexibility it provides processors who might encounter a ready market for xylene but only a lesser demand for benzene. The second is a reduction in the cost for producing a preferred $C_8$ aromatic isomer product. The instant process is cheaper because benzene need not be removed from the methylation zone feed and because benzene in the methylation zone reduces catalyst coking and extends catalyst life.

An unexpected benefit accrues when both benzene and toluene are charged simultaneously to the methylation section in that the benzene acts as a diluent and reduces the concentration of methylating compound required to achieve a particular methylation selectivity at a given methylation conversion. This reduction in methylating compound concentration lessens the rate of three deleterious side reactions: the reaction of the methylating compound with itself, the successive methylation of aromatic-hydrocarbons, and the oligomerization of aromatic hydrocarbons. Both catalyst life and product quality are improved by the presence of benzene as a methylation diluent.

One broad embodiment of the subject invention may be characterized as a process which comprises the steps of charging a feed stream containing $C_2-C_5$ aliphatic-hydrocarbons into a dehydrocyclodimerization zone maintained at dehydrocyclodimerization conditions effective to produce a dehydrocyclodimerization zone effluent stream comprising hydrogen, light hydrocarbons, benzene, toluene, and $C_8+$aromatics; passing the dehydrocyclodimerization zone effluent stream into a first separation zone maintained at conditions effective to separate entering hydrocarbons into a first process stream comprising benzene and toluene, and a second process stream comprising $C_8$ aromatics; methylating a portion of the benzene and toluene in said first process stream with a methylating compound in a methylation zone maintained at methylation conditions effective to produce a methylation zone effluent stream comprising benzene, toluene, and $C_8$ aromatics; returning at least a portion of the methylation zone effluent stream to the first separation zone; passing the second process stream comprising $C_8$ aromatics to a second separation zone maintained at conditions effective to recover a first product stream comprising a preferred $C_8$ aromatic isomer.

A second embodiment of the subject invention may be characterized as a process comprising the steps of charging a feed stream containing $C_2$–$C_5$ aliphatic-hydrocarbons into a dehydrocyclodimerization zone maintained at dehydrocyclodimerization conditions effective to produce a dehydrocyclodimerization zone effluent stream comprising hydrogen, light hydrocarbons, benzene, toluene, and $C_8$+aromatics; passing the dehydrocyclodimerization zone effluent stream into a first separation zone maintained at conditions effective to separate entering hydrocarbons into a first process stream comprising benzene and toluene, a second process stream comprising $C_8$ aromatics, and a third process stream comprising hydrogen; methylating a portion of the benzene and toluene in said first process stream with a methylating compound in a methylation zone maintained at methylation conditions effective to produce a methylation zone effluent stream comprising benzene, toluene, and $C_8$ aromatics; returning at least a portion of the methylation zone effluent stream to the first separation zone; passing the second process stream comprising $C_8$ aromatics to a second separation zone maintained at conditions effective to separate entering hydrocarbons into a first product stream comprising a preferred $C_8$ aromatic isomer and a fourth process stream which is depleted in said preferred $C_8$ aromatic isomer; passing the fourth process stream and at least a portion of the third process stream into an isomerization zone maintained at conditions effective to produce an isomerization zone effluent stream comprising said preferred a $C_8$ aromatic isomer; and, returning at least a portion of the isomerization zone effluent stream to the second separation zone.

BRIEF DESCRIPTION OF THE DRAWING

The two figures are simplified process flow diagrams, each illustrating a preferred embodiment of the invention.

FIG. 2 illustrates all of the features of FIG. 1 and, in addition, illustrates that a stream depleted in the preferred isomer may be taken from the second separation zone 14 via line 16 and introduced into an isomerization zone 17 along with a hydrogen-rich stream shown as line 6. It is preferred that the hydrogen rich stream in line 6 be taken from the first separation zone, but other sources are acceptable. At least a portion of the isomerization zone effluent stream is returned to the second separation zone 14 through line 18.

DETAILED DESCRIPTION

Figure 1:
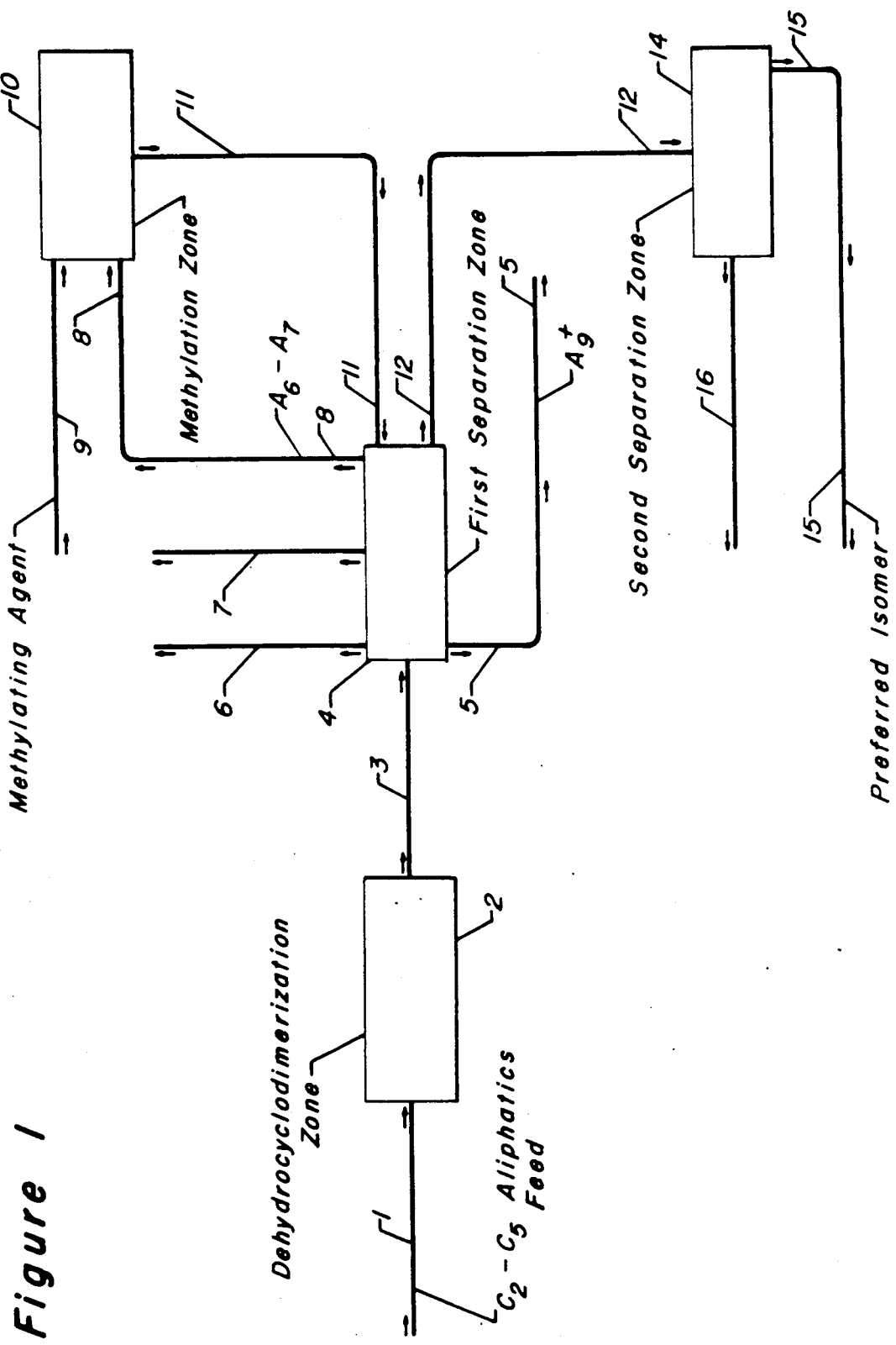
In FIG. 1, light aliphatic hydrocarbons enter through line 1 as feed to the dehydrocyclodimerization (DHCD) zone 2. The partially converted mixture referred to as dehydrocyclodimerization zone effluent 3 enters the first separation zone 4. A stream comprising benzene and toluene 8 enters the methylation zone 10 simultaneously with methylating agent which enters through line 9. The partially converted mixture referred to as methylation zone product 11 is returned to the first separation zone 4. A stream comprising $C_8$ aromatics is taken from the first separation zone 4 through line 12 to a second separation zone 14. A preferred isomer is taken from the second separation zone 14 through line 15.

Petrochemical manufacturers constantly strive to match their production rates of final products to current market demand. The present invention gives manufacturers greater control over product distribution and, therefore, greater flexibility in selecting chargestocks. The object of the invention is to increase the amount of xylene and especially a preferred $C_8$ aromatic isomer product which is produced, without significantly increasing the amount of benzene produced.

The preferred $C_8$ aromatic isomer may be paraxylene, metaxylene, orthoxylene, or ethylbenzene. In the past, however, market demand has most often favored the choice of paraxylene as the preferred $C_8$ aromatic isomer because paraxylene is an important intermediate in the production of terephthalic acid. The individual steps in which the hydrocarbon feeds are converted to other compounds are now reviewed in order to assist in understanding how each contributes to the whole of the invention in the subject process.

The basic aromatics producer in the subject process is the dehydrocyclodimerization step (DHCD), an example of which is the Cyclar process available from UOP. The dehydrocyclodimerization process increases carbon chain length by oligomerization, promotes cyclization, and dehydrogenates cyclics to their respective aromatics. The process operates at a temperature of about 350° to 650° C. and a relatively low pressure of about 10 to 2000 kPa gauge. A particular feature of the process is that large amounts of hydrogen are produced, for example, when propane is oligomerized to the dimer or trimer and then formed into a naphthene, which is dehydrogenated to an aromatic compound. The aromatics are reported to be about 67 wt. % based on the fresh feed and to be mainly benzene and toluene, with smaller amounts of xylenes and heavier aromatics. Cryogenic operations are the preferred method for separating unreacted chargestock from dehydrocyclodimerization products. Fractional distillation is the preferred mode for separating dehydrocyclodimerization aromatic products.

The second basic aromatics conversion step performed in the subject process is methylation of benzene and/or toluene to form xylenes from toluene and toluene from benzene. A methylation process differs from a transalkylation process in that the methylation process transfers a single methyl group from an externally prepared and carefully controlled methylating compound to a chargestock molecule. In contrast, the transalkylation process merely transfers alkyl groups between chargestock molecules present in proportions according to their availability. The methylation process utilizes both the type and concentration of the methylating compound as independent operating variables to control the conversion of the methylation reaction at a given selectivity.

By contacting the benzene and/or toluene with a methylating agent such as methanol or methyl ether, preferably methanol, over a suitable catalyst, toluene and benzene can be converted at a high yield to their homolog with one methyl group added, i.e. xylene and toluene, respectively. This catalyst is normally a crystalline aluminosilicate zeolite. U.S. Pat. Nos. 3,965,208, 4,100,215, and 4,127,616 teach the utility of such compositions in the alkylation of aromatic hydrocarbons and in particular the methylation of toluene. A particularly preferred catalyst for the methylation of toluene with methanol to selectively obtain pary-xylene is a crystalline silica composition which may contain one or more promoters such as arsenic oxide, phosphorous oxide, magnesium oxide, boron oxide, ammonium oxide, amorphous silica, and mixtures thereof. Additional details of this preferred catalyst may be obtained from U.S. Pat. No. 4,444,989.

The methylation of toluene can be carried out in an effective manner by contacting the toluene and methylating agent with a catalyst of the type described above. The reaction is carried out at temperatures ranging from about 750° F. (400° C.) to about 1202° F. (650° C.) and more preferably from about 932° F. (500° C.) to about 1112° F. (600° C.). Pressure conditions within the reaction zone can vary widely with pressures in the range of from about 100 KPa to about 2000 kPa (abs) being preferred. The molar ratio of toluene to methylating agent in the feed can vary from 1:1 to about 1:50. Preferred ratios for operation are in the range of 3:1 to about 20:1 with ratios of 5 to about 15:1 being particularly preferred. The minimum ratio of 1:1 parts toluene to methanol is set to avoid the formation of undesirable by-products in the reaction zone. The higher ratio of 50:1 is set to avoid excessive energy cost in the separation of products from any unreacted toluene feed. Useful weight hourly space velocities for the process can vary from between 1 to 500. The more common space velocity range is between 2 to 250 with about 3 to 100 being particularly preferred. By proper selection of the operating conditions, the type and concentration of the methylating compound, and the catalyst, high yields of the desired products can be obtained.

Recovery of the preferred aromatic isomer from a feed comprising mixed $C_8$ aromatics may be carried out by selective crystallization at low temperatures. Again, the preferred $C_8$ aromatics isomer may be paraxylene, metaxylene, orthoxylene, or ethylbenzene. A single stage of crystallization, followed by a brief treatment with a wash solvent which is later separated from the desired $C_8$ aromatic isomer can produce, for example, paraxylene of 99.2% purity. This method is further described in U.S. Pat. No. 3,916,018. Higher preferred $C_8$ aromatic isomer purities can be obtained by adding additional stages of crystallization or separating the various types of crystals produced by their physical properties, also described in U.S. Pat. No. 3,916,018.

However, a more preferred method of recovering the preferred $C_8$ aromatic isomer is by means of liquid-phase adsorption. X-type zeolitic adsorbents can be used to recover orthoxylene, as described in U.S. Pat. No. 4,529,828, or ethylbenzene, as described in U.S. Pat. No. 4,497,972. A highly preferred method of recovering paraxylene is the Parex process available from UOP. The Parex process uses both x- and y- type zeolites to preferentially adsorb one xylene isomer. A subsequent desorption step is then used to desorb the preferentially absorbed component. The process is effected within the temperature range of 40° C. to about 200° C. within a pressure range of from about atmospheric to about 33,000 kPa as described in U.S. Pat. No. 3,626,020. The fixed bed zeolite adsorbent beds are utilized most efficiently in a continuous flow separation process which periodically changes the location of input and withdrawal points to simulate a moving-bed counter-current process. This may be accomplished with one multi-post stopcock valve ofter referred to as a "rotary valve", as in U.S. Pat. No. 3,310,486, or with a plurality of multipost valves, as in U.S. Pat. No. 4,434,051.

The stream which was depleted in the preferred $C_8$ aromatics isomer may be isomerized. For example, a stream depleted in paraxylene, but rich in orthoxylene, metaxylene, and ethylbenzene may be isomerized to provide additional paraxylene. A desirable isomerization process for $C_8$ aromatics is one which achieves a near equilibrium mixture of xylene isomers in the product with high retention of xylenes. One such process is the Isomar process offered by UOP. The paraxylene-depleted stream is passed along with hydrogen over a suitable catalyst to yield a near-equilibrium quantity of paraxylene, which can be recovered by the processes described above. The requisite hydrogen may be taken from the hydrogen produced in the dehydrocyclodimerization zone, or from another source. The Isomar reaction zone is maintained at proper alkylaromatic isomerization conditions such as a temperature in the range of from about 0° to about 600° C. and a pressure of from atmospheric to about 100-10,000 kPa. Preferably, a temperature range of about 350°-500° C. and a pressure range of 200-3,000 kPa is employed. The hydrocarbon is passed into the reaction zone, preferably in admixture with hydrogen, at a hydrogen to hydrocarbon mole ratio of about 0.5:1 to about 15:1 or more. Other inert diluents such as nitrogen, argon, methane, ethane, and the like may be present. The liquid hourly hydrocarbon space velocity of the feed relative to the volume of catalyst is from about 0.5 to about 30 $hr^{-1}$, and most preferably at 1 to 20 $hr^{-1}$.

In a preferred embodiment of the invention, as depicted in FIG. 1, an aliphatic-hydrocarbon feed stream (1) comprising molecules having from two to five carbon atoms is charged into a dehydrocyclodimerization zone (2). The aliphatic-hydrocarbon source could be liquified petroleum gas or a light hydrocarbon stream separated from crude petroleum or light hydrocarbon produced as a by-product of another chemical process, such as hydrocracking. The feed stream to the dehydrocyclodimerization process is defined as all streams introduced into the dehydrocyclodimerization reaction zone with the exception of the methylating agent stream. Included in the feed stream is the $C_2$-$C_5$ aliphatic hydrocarbon. By $C_2$-$C_5$ aliphatic hydrocarbon is meant one or more open, straight or branched chain isomers having from two to five carbon atoms per molecule. Furthermore, the hydrocarbons in the feedstock may be saturated or unsaturated. Preferably, the hydrocarbons $C_3$ and/or $C_4$ are selected from isobutane, normal butane, isobutene, normal butene, propane and propylene. Diluents may also be included in the feed stream. Examples of such diluents include hydrogen, nitrogen, helium, argon, neon, CO, $CO_2$, $H_2O$ or its precursors. Water precursors are defined as those compounds which liberate $H_2O$ when heated to dehydrocyclodimerization reaction temperatures.

The dehydrocyclodimerization conditions which will be employed for use with the catalyst composition of the present invention will, of course, vary depending on such factors as feedstock composition and desired conversion. A desired range of conditions for the dehydrocyclodimerization of $C_2$-$C_5$ aliphatic hydrocarbons to aromatics include a temperature from about 350° C. to about 650° C., a pressure from about 1 to about 20 atmospheres, and a liquid hourly space velocity from about 0.2 to about 5 $hr^{-1}$. The preferred process conditions are a temperature in the range from about 400° to 550° C., a pressure in the range from 2 to 10 atmospheres and a liquid hourly space velocity of between 0.5 to 2.0 $hr^{-1}$. It is understood that, as the average carbon number of the feed increases, a temperature in the lower end of temperature range is required.

According to the present invention, the feed stream is contacted with the instant catalytic composite in the dehydrocyclodimerization reaction zone maintained at dehydrocyclodimerization conditions. This contacting may be accomplished by using the catalytic composite in a fixed bed system, a moving bed system, a fluidized bed system, or in a batch type operation. In view of the danger of attrition losses of the valuable catalyst and of the well known operational advantages, it is preferred to use either a fixed bed system or a dense-phase moving bed system such as shown in U.S. Pat. No. 3,725,249.

The dehydrocyclodimerization zone comprises a catalyst. A preferred type of dehydrocyclodimerization catalyst comprises a gallium component and a crystalline aluminosilicate zeolite having a silica to alumina ratio of at least 12 incorporated with a phosphorous-containing alumina. Such a catalyst is described in U.S. Pat. No. 4,636,483 which is herein incorporated by reference. It is believed that this phosphorous-containing alumina is directly responsible for observed reduced catalyst coke levels. Because the dehydrocyclodimerization reaction is often carried out in the absence of added hydrogen in order to obtain a favorable reaction equilibrium, the reduced coking tendency which phosphorous-containing alumina promotes is an important attribute. A preferred catalyst is the ZSM-5 type zeolite treated with nitrogen-based agents such as nitrogen dioxide and ammonia. The preparation and use of such catalyst are further described in U.S. Pat. No. 4,477,584. The catalyst can be regenerated by means such as those described in U.S. Pat. Nos. 4,724,721 and 4,795,845.

It is, of course, understood that the dehydrocyclodimerization zone may be one or more separate reactors with suitable means to assure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, admixed liquid-vapor phase, or a vapor phase when they contact the catalyst, with the best result obtained in the vapor phase.

Referring to FIG. 1, a dehydrocyclodimerization effluent stream (3) is produced in the dehydrocyclodimerization zone and passed to a first separation zone (4). A methylation zone effluent stream (11), produced in the methylation zone (10), is also passed to the first separation zone. In an especially preferred embodiment, the first separation zone would include heat transfer equipment to cool the stream, a separator vessel to remove uncondensible gases (6) such as hydrogen, and one or more fractional distillation columns.

The first separation zone (4) produces a first process stream comprising benzene and toluene (8) which is passed to the methylation zone (10), and a second process stream comprising eight-carbon aromatics (12) which is passed to the second separation zone (14). The $C_9+$ aromatics are removed as a separate stream (5). Net benzene and the bulk of the $C_6$-minus hydrocarbons can be removed as a single stream (7) or further subdivided. The fact that benzene need not be separated from the toluene in the second process stream is another economic advantage of this process. Alternatively, benzene and other $C_6$-minus components may be recycled to the dehydrocyclodimerization reaction zone according to the teachings of U.S. Pat. No. 4,642,402 which is herein incorporated by reference.

The second process stream (8) is further processed in the methylation zone (10) in the presence of a methylating agent (9) such as methanol or methyl ether. The methylating agent may be mixed directly in the second process stream, injected into the methylation zone through a separate line, or simultaneously introduced at several different points within the reaction zone.

Both the molar ratio of methylating agent to toluene and the partial pressure of the methylating agent are strong methylation zone operating variables. A higher concentration of methylating agent will promote a higher methylation conversion of the second process stream, but increased methylating agent partial pressure which accompanies high methylating agent concentration will promote undesirable reactions such as reaction of the methylation agent with itself, oligomerization of benzene and toluene, and repeated poly-methylation of toluene. Suprisingly, the presence of benzene in the second process stream allows higher methylation conversion with less of the undesirable reaction products. The benzene acts as a diluent to reduce the partial pressure of methylating agent at a given methylating agent to toluene ratio. Further, the benzene diluent does not increase the long-term rate of catalyst deactivation as would steam diluent.

All of the benzene in the dehydrocyclodimerization reaction zone effluent stream may be taken as net product. Alternatively, a portion of the benzene may be passed into the methylation zone to serve as a diluent (8). It is preferred that the concentration of benzene in the methylation zone feed stream be within the range of 10% to 50% by volume, with concentrations from 20% to 30% being especially preferred. Other diluents such as hydrogen, nitrogen, $C_1$-$C_6$ paraffins, or steam may be utilized simultaneously with the benzene diluent. It is preferred that the total amount of said other diluents be present within the range of feed mixture for the methylation zone from about 10% to 50% by volume. An especially preferred feed mixture for the methylation zone comprises 25 mol % benzene and 10 mol % steam. Approximately 20% of the benzene in the methylation zone feed will be converted to toluene in a single pass through the methylation zone and the balance can be recycled (11) via the first separation zone (4). In a preferred embodiment, the amount of recycled benzene is adjusted so that from 30% to 50% of the benzene in the dehydrocyclodimeization zone effluent stream is converted to other compounds in the methylation zone.

The second process stream (12) is passed to the second separation zone (14) which comprises means for recovering a first product stream (15) which is rich in a preferred isomer relative to the thermal equilibrium value for that isomer. A fourth product stream (16) comprising less desirable components of the second product stream can be sent elsewhere for further processing or disposal. Preferred means for recovering the preferred isomer are adsorption and fractional crystallization. In many cases, the preferred isomer will be paraxylene. An especially preferred means of recovering paraxylene is the UOP Parex TM process which utilizes a plurality of solid adsorbent beds sequentially staged to simulate a continuous adsorption separation process.

In an especially preferred embodiment of the invention, as depicted in FIG. 2, the fourth product stream (16) is further processed in the isomerization zone (17). There, it may be contacted with hydrogen in the presence of a catalyst in order to produce an isomerization zone effluent stream (13) rich in the preferred $C_8$ aromatic isomer which is returned to the second separation zone. The source of hydrogen for isomerization may be the non-condensible gas stream (6) produced by the first separation zone.

For a better understanding of the present invention, three paper examples follow which present expected product yields predicted for three operating modes of the embodiment illustrated in FIG. 2. Note that the propane or butane feedstream would be dehydrocyclodimerized to produce toluene which would be subsequently methylated to produce the preferred $C_8$ aromatic isomer and some by-products. In the following examples, the preferred $C_8$ aromatic isomer is paraxylene. If the type and amount of feed labeled as propane in Examples A and C, and butane in Example B, of Table 1 were sent through line 1 of FIG. 2, and the corresponding amount and type of methylating agent labeled as methanol were sent through line 9 of FIG. 2, and the reaction zones were maintained at the preferred conditions disclosed above, the expected product yields would be:

TABLE 1

MATERIAL BALANCES FOR AROMATIC COMPLEXES INCLUDING DEHYDROCYCLODIMERIZATION AND SELECTIVE TOLUENE METHYLATION

| Example | A | B | C |
|---|---|---|---|
| FEEDSTREAM, KMTA | | | |
| Propane | 411.0 | — | 411.0 |
| Butanes | — | 355.0 | — |
| METHYLATING AGENT, KMTA | | | |
| Methanol | 70.5 | 65.9 | 109.9 |
| TOTAL INFLUENT | 481.5 | 420.9 | 520.9 |
| PRODUCTS, KMTA | | | |
| Para-xylene | 153.0 | 152.9 | 194.4 |
| Benzene | 82.2 | 58.9 | 47.6 |
| Hydrogen* | 32.0 | 24.5 | 32.0 |
| Light Ends | 137.9 | 115.2 | 143.1 |
| Water | 39.7 | 37.1 | 61.9 |
| Heavies | 36.7 | 32.3 | 41.9 |
| TOTAL EFFLUENT | 481.5 | 420.9 | 520.9 |

*At 95 mol-% purity

The product rates for Examples A and B were calculated under the assumption that all of the benzene in the dehydrocyclodimerization reaction zone effluent stream would be taken as net product and that only toluene would be passed to the methylation zone. Example C was calculated for a methylation feed which comprised 25 mol % benzene and 10% steam or other diluent.

Clearly, the ratio of paraxylene to benzene in the final products would tend to vary, depending on the composition of the feed stream to the methylation zone. However, the production rate of the preferred isomer, which is paraxylene in these examples, as compared to the benzene production rate would be controllable and the manufacturer could adjust the two to match his market demand by controlling the amount of benzene removed from the system via line 7.

By way of illustration, a petrochemical manufacturer operating at the conditions of Example A might find it profitable to produce more para-xylene but have no market for additional benzene. By withdrawing less net benzene from the first separation zone, such a manufacturer could approach the conditions of Example C and optimize his total product slate.

What is claimed:

1. A process for producing benzene and xylenes enriched in a $C_8$ isomer comprising:
   (a) charging a feed stream comprising a $C_2$–$C_5$ aliphatic hydrocarbon into a dehydrocyclodimerization zone maintained at dehydrocyclodimerization conditions effective to produce a dehydrocyclodimerization zone effluent stream comprising hydrogen, light hydrocarbons, benzene, toluene, and $C_8{}^+$ aromatics;
   (b) passing the dehydrocyclodimerization zone effluent stream into a first separation zone maintained at conditions effective to separate entering hydrocarbons into a first process stream comprising benzene and toluene, and a second process stream comprising $C_8$ aromatics;
   (c) methylating a portion of the benzene and toluene in said first process stream with a methylating compound in a methylation zone maintained at methylation conditions effective to produce a methylation zone effluent stream comprising benzene, toluene, and $C_8$ aromatics;
   (d) returning at least a portion of the methylation zone effluent stream to the first separation zone;
   (e) passing the second process stream comprising $C_8$ aromatics to a second separation zone maintained at conditions effective to recover a first product stream comprising said $C_8$ aromatic isomer.

2. The process of claim 1 further characterized in that the first separation zone comprises a liquid-vapor separator and a fractional distillation column.

3. The process of claim 1 further characterized in that said first process stream comprises about 10% to 50% benzene by volume.

4. The process of claim 3 further characterized in that said first process stream comprises about 10% to 50% by volume of one or more diluent gases selected from the group consisting of steam, hydrogen, nitrogen, and $C_1$ to $C_6$ paraffins.

5. The process of claim 3 further characterized in that about 30% to 50% of the benzene produced in the dehydrocyclodimerization zone is converted in the methylation zone.

6. The process of claim 3 further characterized in that the methylating compound comprises methanol or methyl ether.

7. A process for producing benzene and xylenes enriched in a $C_8$ isomer comprising:
   (a) charging a feed stream containing a $C_2$–$C_5$ aliphatic hydrocarbon into a dehydrocyclodimerization zone maintained at dehydrocyclodimerization conditions effective to produce a dehydrocyclodimerization zone effluent stream comprising hydrogen, light hydrocarbons, benzene, toluene, and $C_8$+aromatics;
   (b) passing the dehydrocyclodimerization zone effluent stream into a first separation zone maintained at conditions effective to separate entering hydrocarbons into a first process stream comprising benzene and toluene, a second process stream comprising $C_8$ aromatics, and a third process stream comprising hydrogen;
   (c) methylating a portion of the benzene and toluene in said first process stream with a methylating compound in a methylation zone maintained at methylation conditions effective to produce a methylation zone effluent stream comprising benzene, toluene, and $C_8$ aromatics;
   (d) returning at least a portion of the methylation zone effluent stream to the first separation zone;
   (e) passing the second process stream comprising $C_8$ aromatics to a second separation zone maintained at conditions effective to separate entering hydrocarbons into a first product stream comprising said C$_8$ aromatic isomer and a fourth process stream which is depleted in said C$_8$ aromatic isomer;

(f) passing the fourth process stream and at least a portion of the third process stream from (b) into an isomerization zone maintained at conditions effective to produce an isomerization zone effluent stream comprising said C$_8$ isomer; and, (g) returning at least a portion of the isomerization zone effluent stream to the second separation zone of step (e).

8. The process of claim 7 further characterized in that the first separation zone comprises a liquid-vapor separation and a fractional distillation column.

9. The process of claim 7 further characterized in that said first process stream comprises about 10% to 50% benzene by volume.

10. The process of claim 9 further characterized in that said first process stream comprises about 10% to 50% by volume of one or more diluent gases selected from the group consisting of steam, hydrogen, nitrogen, and C$_1$ to C$_6$ paraffins.

11. The process of claim 9 further characterized in that about 30% to 50% of the benzene in the dehydrocyclodimerization zone effluent stream is converted in the methylation zone.

12. The process of claim 9 further characterized in that the methylating compound comprises methanol or methyl ether.

13. The process of claim 7 further characterized in that the second separation zone comprises liquid-phase adsorption.

14. The process of claim 7 further characterized in that the second separation zone comprises selective crystallization.

* * * * *